(12) United States Patent
Turnbaugh, Jr. et al.

(10) Patent No.: US 7,182,931 B2
(45) Date of Patent: Feb. 27, 2007

(54) PROCESS FOR MAKING TITANIUM DIOXIDE

(75) Inventors: Donald Theodore Turnbaugh, Jr., Oklahoma City, OK (US); Bruce Lynn Roberts, Norman, OK (US)

(73) Assignee: Tronox LLC, Oklahoma City, OK (US)

( * ) Notice: Subject to any disclaimer, the term of this patent is extended or adjusted under 35 U.S.C. 154(b) by 494 days.

(21) Appl. No.: 10/374,266

(22) Filed: Feb. 25, 2003

(65) Prior Publication Data

US 2004/0166054 A1 Aug. 26, 2004

(51) Int. Cl.
*C01G 23/047* (2006.01)

(52) U.S. Cl. ..................................... 423/613

(58) Field of Classification Search ............... 423/613, 423/614, DIG. 5; 106/437
See application file for complete search history.

(56) References Cited

U.S. PATENT DOCUMENTS 3,481,697 A * 12/1969 Figuet et al. ................. 423/79
5,670,121 A * 9/1997 Elkins .......................... 423/74
6,207,131 B1 * 3/2001 Magyar et al. ............. 423/613

FOREIGN PATENT DOCUMENTS

EP 654446 * 5/1995

OTHER PUBLICATIONS

On-line Process Analyzers, Nichols, 1988,no month, p. 3-7; 117-119; 239; 243-244.
Vol I, Pigment Handbook, Lewis, 1988,no month, p. 14-15.
Vol 24, 4TH Ed., Kirk-Othmer, 1997,no month, p. 244-248.

* cited by examiner

*Primary Examiner*—Steven Bos
(74) *Attorney, Agent, or Firm*—Timothy S. Stevens

(57) ABSTRACT

An improved process for producing titanium dioxide by reacting a titanium dioxide ore with chlorine to produce a gaseous stream containing titanium tetrachloride, condensing titanium tetrachloride from the gaseous stream containing titanium tetrachloride to produce chlorinator tail gas, vaporizing the condensed titanium tetrachloride, reacting the vaporized titanium tetrachloride with oxygen to produce a gaseous stream containing titanium dioxide particles and chlorine, separating the titanium dioxide particles from the gaseous stream containing titanium dioxide particles and chlorine to produce burner tail gas, analyzing the chlorinator tail gas for residual chlorine to control the step of reacting the titanium dioxide ore with chlorine, analyzing the burner tail gas for oxygen to control the step of reacting the condensed titanium tetrachloride with oxygen. The improvement is to analyze the chlorinator tail gas for residual chlorine (and/or the burner tail gas for oxygen) using an on-line analyzer.

7 Claims, 5 Drawing Sheets

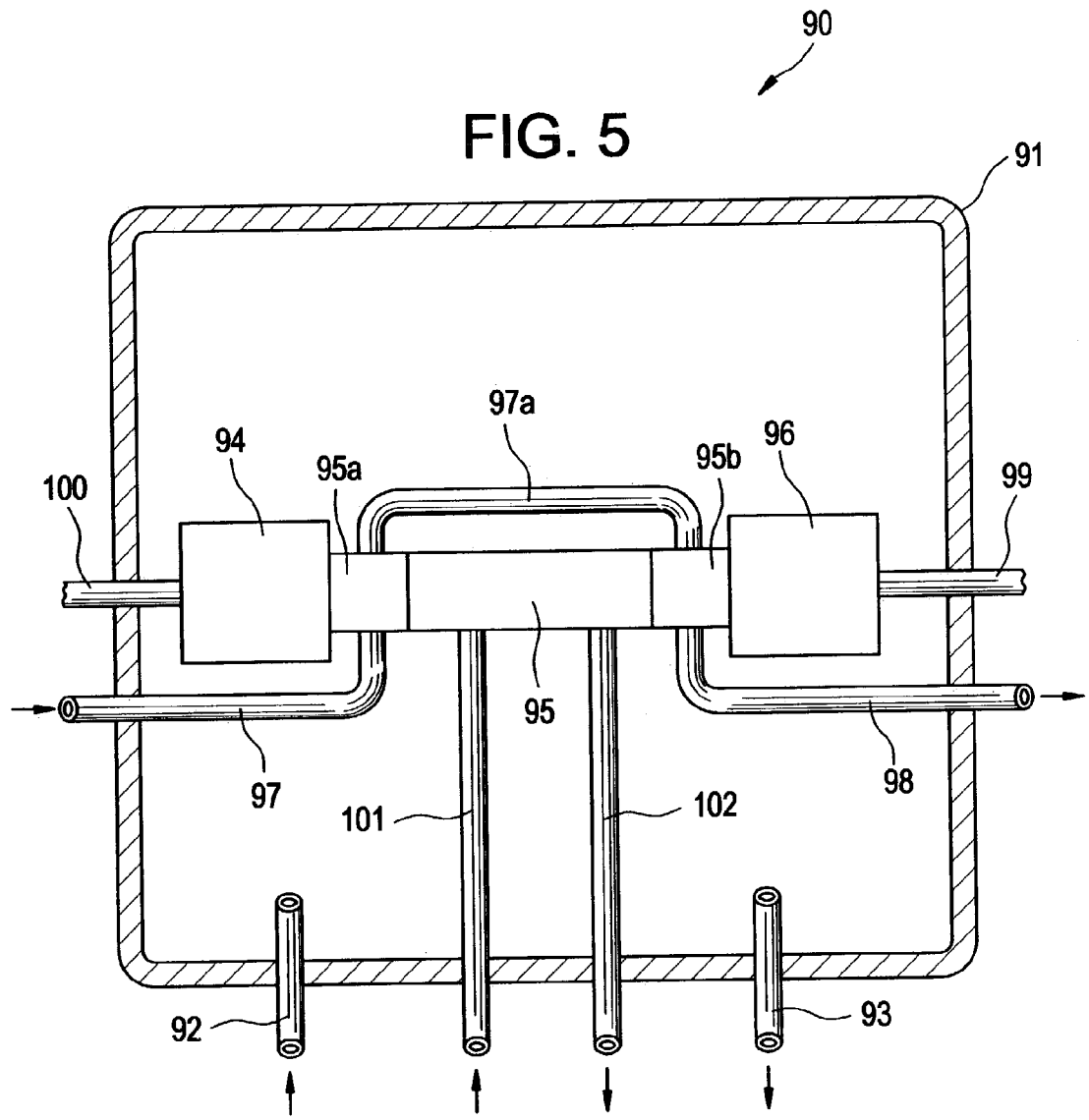

PROCESS FOR MAKING TITANIUM DIOXIDE

BACKGROUND

Referring now to FIG. 1, in the known chloride process 10 for making titanium dioxide, a source of crude titanium dioxide (e.g., rutile ore) from hopper 11 is first reacted with chlorine from chlorine tank 12 and carbon (e.g., coke) from carbon hopper 13 in a chlorinator 14 to produce a gaseous stream 15 containing primarily titanium tetrachloride, carbon monoxide and carbon dioxide but also dust particles and other impurities. The titanium tetrachloride is condensed from stream 15 by condenser 16, purified by distillation, vaporized and then directed to burner 17 where the titanium tetrachloride is reacted with oxygen from oxygen tank 18 to produce a gaseous stream 19 containing primarily particulate titanium dioxide and chlorine gas.

A "support fuel", (not shown) such as propane gas, can also be introduced into the burner 17 to increase the temperature in the burner 17. The stream 19 is then cooled in cooler 20 and then the particulate titanium dioxide is separated from the chlorine gas by gas/solids separator 21. The particulate titanium dioxide is then directed from gas/solids separator 21 to surface treatment tank 22 for further processing. The gaseous chlorine stream 25 from the gas/solids separator 21 is directed to a chlorine compressor 26 for recycle to the chlorinator 14. The gaseous chlorine stream 25 is called "burner tail gas". The carbon monoxide, carbon dioxide, dust and other impurities from the condenser 16, called "chlorinator tail gas" 23 is treated by treatment system 24 to remove undesirable components (such as residual chlorine and carbon monoxide) and then vented.

The particulate titanium dioxide produced by the chloride process is used, for example, as a pigment in paints. A more detailed discussion of the chloride process for producing titanium dioxide can be found in Volume 24 of the Kirk-Othmer Encyclopedia of Chemical Technology ($4^{th}$ Ed., 1997) and in Volume I of the Pigment Handbook, Edited by Lewis ($2^{nd}$ Ed., 1988).

Referring still to FIG. 1, chemical analysis of the chlorinator tail gas 23 for residual chlorine allows for more effective control of the chlorinator 14. For example, if an excessive amount of chlorine is fed to the chlorinator 14, then the chlorinator tail gas 23 will contain relatively high levels of chlorine to be treated by treatment system 24. Therefore, samples of the chlorinator tail gas are periodically taken to a laboratory and analyzed for chlorine to better control the chlorinator 14. Similarly, chemical analysis of the burner tail gas 25 for oxygen allows for more effective control of the burner 17. For example, if an excessive amount of oxygen is fed to the burner 17, the excessive oxygen is wasted. Therefore, samples of the burner tail gas 25 are periodically taken to a laboratory and analyzed for oxygen. The burner tail gas 25 can also be analyzed for hydrogen chloride since the hydrogen chloride concentration of the burner tail gas 25 is a function of the amount of support fuel used in the burner 17. Frequent sampling and analysis of the chlorinator tail gas 23 and the burner tail gas 25 are desired for close control of the chlorinator 14 and the burner 17. However, manual sampling and analysis of the chlorinator tail gas 23 and the burner tail gas 25 is labor intensive, relatively expensive and limits process control.

SUMMARY OF THE INVENTION

The instant invention, to a large degree, provides an effective solution to the above discussed problems. In the instant invention the chlorinator tail gas and/or the burner tail gas are analyzed on-line thereby providing continuous automated analysis.

In one embodiment the instant invention is an improved process for producing titanium dioxide by reacting a titanium dioxide ore with chlorine to produce a gaseous stream containing titanium tetrachloride, condensing titanium tetrachloride from the gaseous stream containing titanium tetrachloride to produce chlorinator tail gas, vaporizing the condensed titanium tetrachloride, reacting the vaporized titanium tetrachloride with oxygen to produce a gaseous stream containing titanium dioxide particles and chlorine, separating the titanium dioxide particles from the gaseous stream containing titanium dioxide particles and chlorine to produce burner tail gas, and analyzing the chlorinator tail gas for residual chlorine to control the step of reacting the titanium dioxide ore with chlorine, wherein the improvement comprises the step of: analyzing the chlorinator tail gas for residual chlorine using an on-line chlorine analyzer.

In another embodiment the instant invention is also an improved process for producing titanium dioxide by reacting a titanium dioxide ore with chlorine to produce a gaseous stream containing titanium tetrachloride, condensing titanium tetrachloride from the gaseous stream containing titanium tetrachloride to produce chlorinator tail gas, vaporizing the condensed titanium tetrachloride, reacting the vaporized titanium tetrachloride with oxygen to produce a gaseous stream containing titanium dioxide particles and chlorine, separating the titanium dioxide particles from the gaseous stream containing titanium dioxide particles and chlorine to produce burner tail gas, and analyzing the burner tail gas for oxygen to control the step of reacting the vaporized titanium tetrachloride with oxygen, wherein the improvement comprises the step of: analyzing the burner tail gas for residual oxygen using an on-line oxygen analyzer.

In yet another embodiment the instant invention is a process for conditioning chlorinator tail gas or burner tail gas from a chloride process for making titanium dioxide. Components (such as particulates and sludge) that tend interfere with on-line analysis of the chlorinator tail gas or the burner tail gas are sufficiently removed using this embodiment of the instant invention so that the measurement accuracy, reliability and service life of an on-line analyzer is significantly increased. This embodiment of the instant invention comprises three steps. The first step is to flow chlorinator tail gas or burner tail gas from a chloride process for making titanium dioxide through a bed of glass wool to produce a primary treated stream. The second step is to flow the primary treated stream through a submicron particulate filter to produce a secondary treated stream. The third step is to flow the secondary treated stream through a coalescing filter to produce a conditioned gas stream to be directed to an on-line chemical analyzer(s).

BRIEF DESCRIPTION OF THE DRAWINGS

FIG. 5 a side view, part in full, part in cross section and part schematic, of an apparatus for on-line analysis of chlorinator tail gas for chlorine.

DETAILED DESCRIPTION OF PREFERRED EMBODIMENTS OF THE INVENTION

Figure 2:
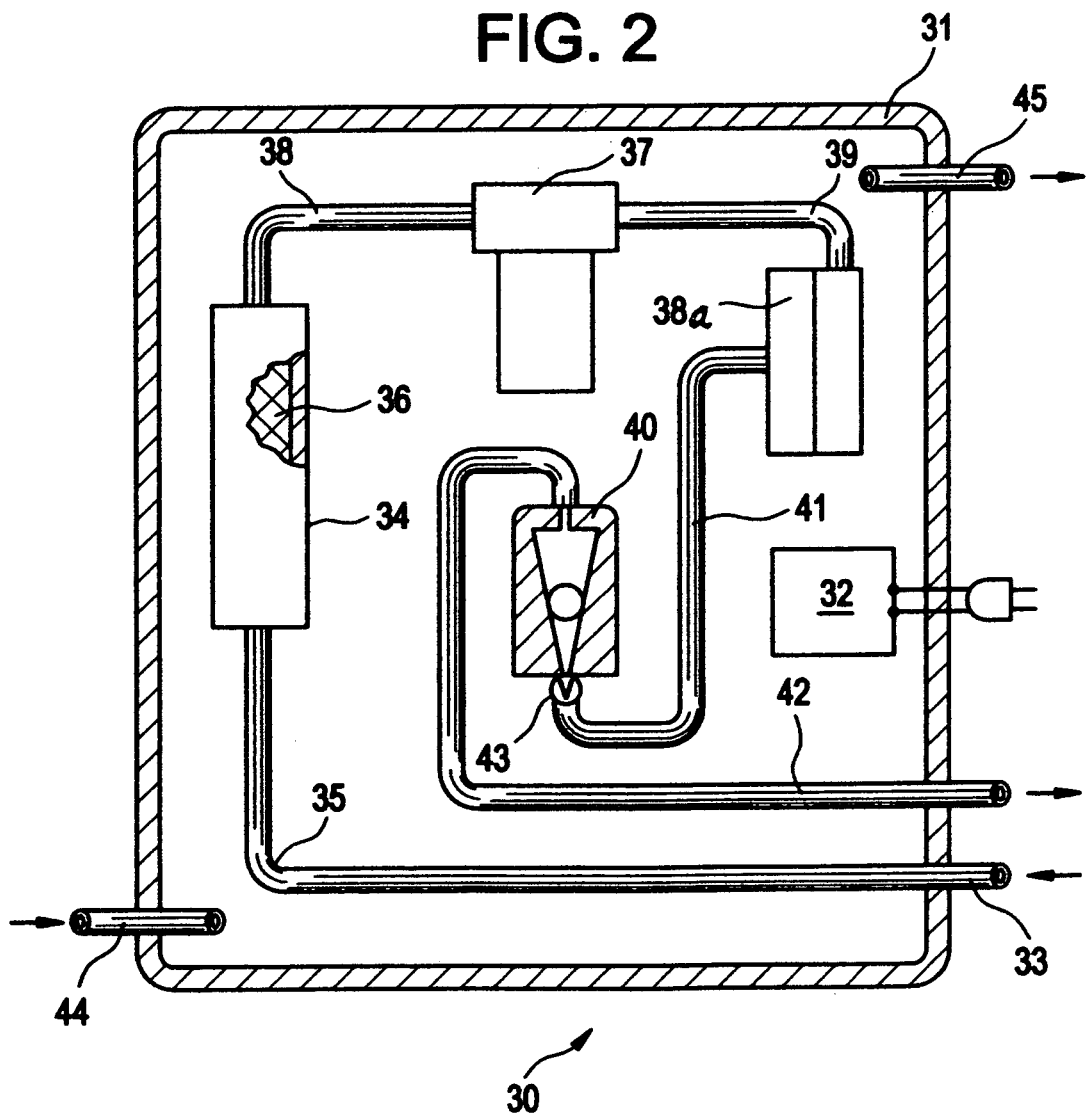
FIG. 2 is side view, part in full, part broken away, part in cross-section and part schematic, of an apparatus for conditioning chlorinator tail gas or burner tail gas prior to on-line analysis.

Referring now to FIG. 2, therein is shown an apparatus 30 for conditioning chlorinator tail gas or burner tail gas from a chloride process for making titanium dioxide. The apparatus 30 includes an enclosure 31 (preferably being a NEMA-4 fiberglass enclosure, Hoffman Co., Anoka Minn.) heated by a thermostated (at one hundred degrees Fahrenheit) four hundred watt electric heater 32 (Hoffman Co., Anoka Minn.). Chlorinator tail gas or burner tail gas is conducted to the apparatus 30 by way of tubing 33 (preferably 0.375 inch outside diameter, 0.060 inch wall thickness, heat traced (at about ninety degrees Celsius) perfluoroalkoxy tubing).

The chlorinator tail gas or burner tail gas is then conducted to a one and one half inch diameter by fifteen inch long glass column 34 (part number 5820-53 & 5844-78, Ace Glass Co., Vineland N.J.) by one quarter inch diameter perfluoroalkoxy tubing 35 (part number U-06375-75, Cole Parmer, Vernon Hills Ill.). The column 34 is packed with glass wool 36 (preferably, Pyrex Brand glass wool, product number Z25, 589-0 from Sigma Aldrich, St. Louis, Mo.). The chlorinator tail gas or burner tail gas flows through the glass wool 36 to produce a primary treated stream conducted to a submicron filter 37 by way of one quarter inch diameter perfluoroalkoxy tubing 38. The glass wool 36 removes the larger particulates from the chlorinator tail gas or burner tail gas stream and provides a high surface area for deposition of sludge.

The submicron filter 37 is a filter that removes particles from the primary treated stream that are smaller than one micron in size (preferably a United Filtration System, Sterling Heights Mich., borosilicate glass fiber/fluorocarbon binder submicron filter) to produce a secondary treated stream conducted to a coalescing filter 38a by way of one quarter inch diameter perfluoroalkoxy tubing 39. The secondary treated stream flows through the coalescing filter 38a (preferably a Genie Brand coalescing filter from A+ Corporation of Prairieville La.) to produce a conditioned gas stream that is flowed to a rotameter 40, through metering valve 43, by way of one quarter inch diameter perfluoroalkoxy tubing 41.

The coalescing filter 38a removes aerosol mists that passed through the glass wool 36 and the submicron filter 37. The rotameter 40 (preferably part number U-03216-75 from Cole Parmer, Vernon Hills Ill.) is used to measure the flow rate of the conditioned gas stream. A substantial reduction of the flow rate of the conditioned gas stream probably indicates that the glass wool 36 needs to be replaced (or possibly that the submicron filter 37 needs to be replaced). The conditioned gas stream is conducted to an on-line analyzer by way of heat traced (at about ninety degrees Celsius) one quarter inch diameter perfluoroalkoxy tubing 42. Tubing 44 is used to conduct a nitrogen purge stream into the enclosure 31. Tubing 45 is used to conduct the nitrogen purge stream from the enclosure 31.

The heater 32 is most preferably set to control the temperature in the enclosure 31 to be preferably greater than fifty degrees Fahrenheit. When the conditioning process of the instant invention is operated at a temperature below fifty degrees Fahrenheit, plugging and sludge formation may occur due to condensation. Thus, more preferably, the temperature in the enclosure 31 is set to be more than seventy degrees Fahrenheit. Most preferably, the temperature in the enclosure 31 is set to be in the range of from ninety to one hundred and ten degrees Fahrenheit. Heating the enclosure 31 (and thus the conditioning process of the instant invention) helps prevent the formation of sludge and significantly increases the service life of the conditioning system (and, of course, the on-line analyzers) and the need to replace plugged tubing and filters.

It should be understood that the above description relates to a specific apparatus for conditioning chlorinator tail gas or burner tail gas and that the full scope of the instant invention is not limited thereby. For example, although the above specified glass wool performs well in the process of the instant invention, other types of glass wool can be used. Similarly, other types of submicron filters can be used as well as other types of coalescing filters, such as the wide range of submicron and coalescing filters available from United Filtration Systems, Sterling Heights Mich. Furthermore, it should be understood that any suitable filter system can be used in the instant invention.

Preferably, the apparatus 30 can also include a differential pressure transducer(s) (not shown) to measure the pressure drop across the column 34, the submicron filter 37 and/or the coalescing filter 38a to better determine if the column 34, the submicron filter 37 or the coalescing filter 38a are becoming plugged and need replacement. Preferably, a tubing tee and shut-off valve (not shown) are installed in the tubing 35 so that the flow of chlorinator tail gas or burner tail gas can be temporarily shut off so that nitrogen gas can be flowed through the apparatus 30 at a calibrated flow rate. A pressure transducer (not shown) can be installed to measure the pressure in the tubing 41. If the conditioned gas stream is to be directed to more than one on-line analyzer, then the conditioned gas stream can be split and a rotameter (or other flow measuring device or no such device or devices if desired) used for each such on-line analyzer.

Figure 3:
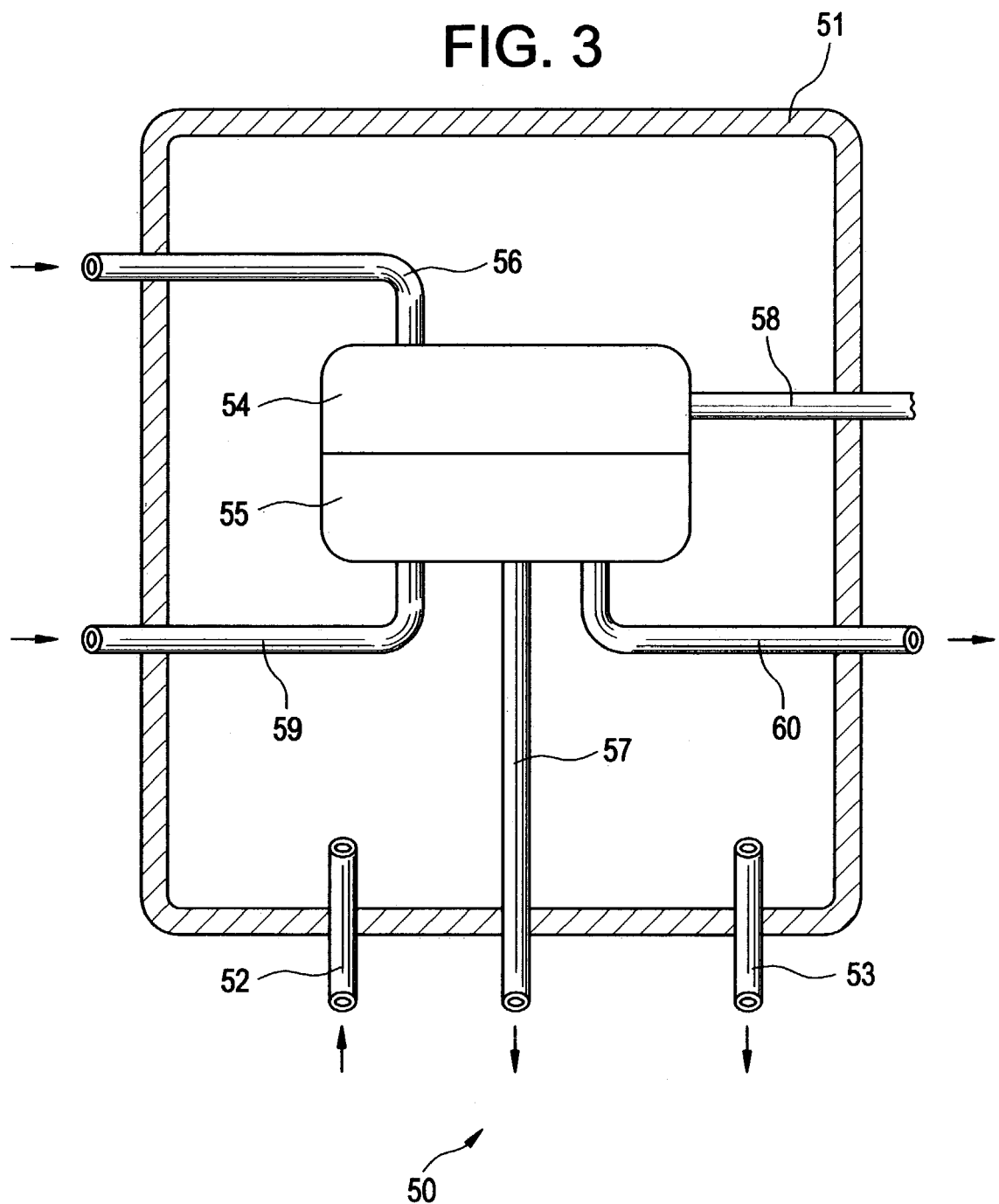
FIG. 3 is a side view, part in full, part in cross section and part schematic, of an apparatus for on-line analysis of burner tail gas for oxygen.

Referring now to FIG. 3, therein is shown a side view, part in full, part in cross section and part schematic, of an apparatus 50 for on-line analysis of burner tail gas for oxygen. The apparatus 50 includes an enclosure 51 (preferably a NEMA-4 fiberglass enclosure, supra). Tubing 52 is used to conduct a nitrogen purge stream into the enclosure 51. Tubing 53 is used to conduct the nitrogen purge stream from the enclosure 51. The enclosure 51 contains a Siemens Oxymat 6F-$O_2$ paramagnetic oxygen analyzer comprised of an electronics portion 54 and a cell portion 55. Tubing 56 is used to conduct a nitrogen purge stream into the electronics portion 54. This nitrogen purge stream then flows through the cell portion 55 and out of the enclosure 51 by way of tubing 57. Electrical cable 58 provides power to the electronics portion 54 as well as conducting an analyzer signal from the apparatus 50, which signal is a function of the oxygen concentration in the burner tail gas. Conditioned burner tail gas (from the apparatus shown in FIG. 2) is conducted to and from the cell portion 55 by way of one quarter inch diameter heat traced (at about ninety degrees Celsius) perfluoroalkoxy tubing 59 and 60 respectively.

Figure 4:
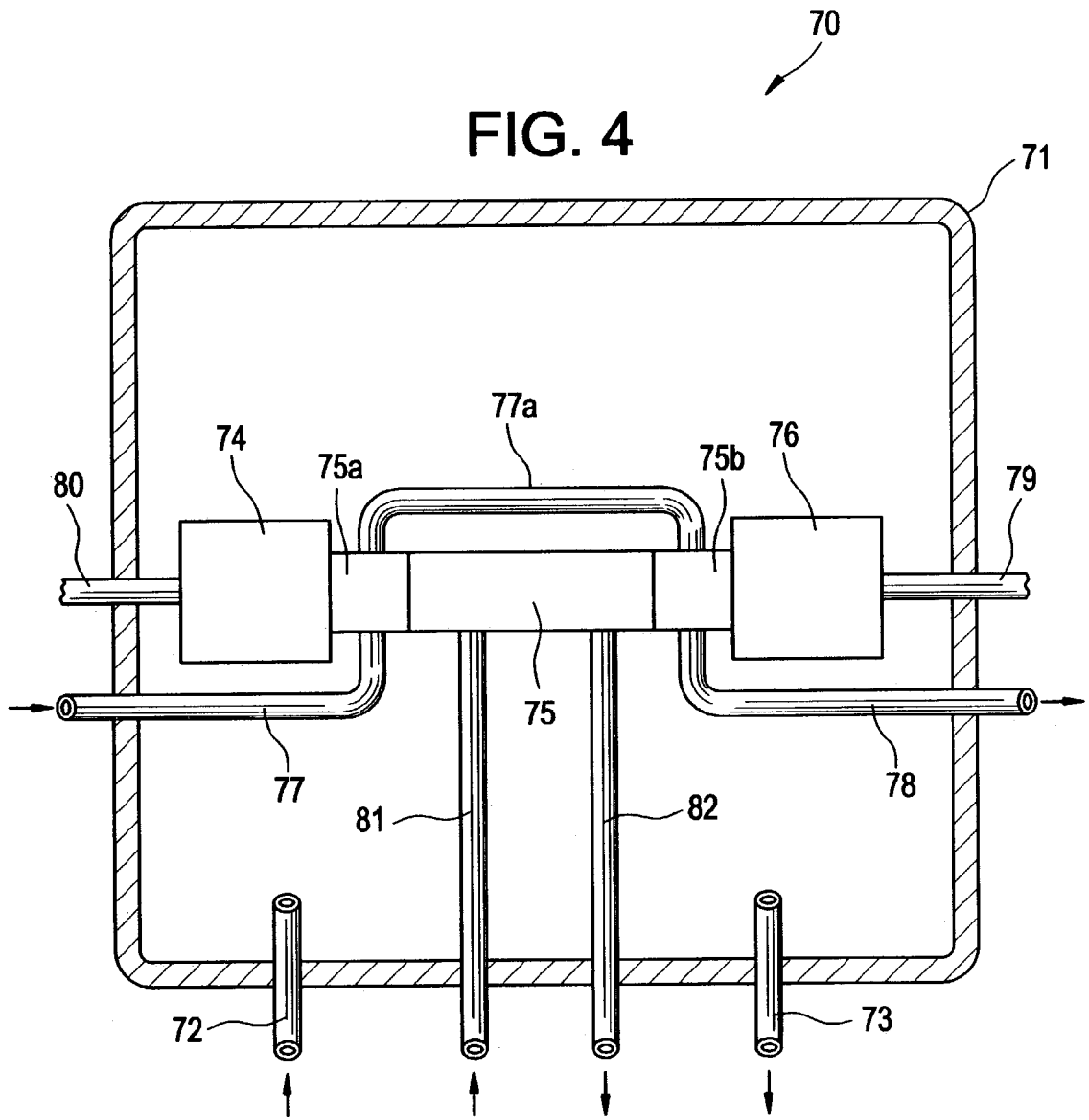
FIG. 4 is a side view, part in full, part in cross section and part schematic, of an apparatus for on-line analysis of burner tail gas for hydrogen chloride.

Referring now to FIG. 4, therein is shown a side view, part in full, part in cross section and part schematic, of an apparatus 70 for on-line analysis of burner tail gas for hydrogen chloride. The apparatus 70 includes an enclosure 71 (preferably a NEMA-4 fiberglass enclosure, supra). Tubing 72 is used to conduct a nitrogen purge stream into the enclosure 71. Tubing 73 is used to conduct the nitrogen purge stream from the enclosure 71. The enclosure 71 contains a Servomex Xendos 2500 HCl infrared analyzer (Servomex Company Inc., Sugarland, Tex.) comprised of a detector portion 74, a cell portion 75 and a source portion 76. Tubing 77 is used to conduct a nitrogen purge stream through a boss 75a, then through boss 75b by way of tubing 77a and then out of the enclosure 71 by way of tubing 78. The boss portions 75a and 75b of the cell 75 help protect the detector portion 74 and the source portion 76 from leaks. Electrical cables 79 and 80 provide power to and conduct an analyzer signal from the apparatus 70, which signal is a function of the hydrogen chloride concentration in the burner tail gas. Conditioned burner tail gas (from the apparatus shown in FIG. 2) is conducted to and from the cell portion 75 by way of one quarter inch diameter heat traced (at about ninety degrees Celsius) perfluoroalkoxy tubing 81 and 82 respectively.

Referring now to FIG. 5, therein is shown a side view, part in full, part in cross section and part schematic, of an apparatus 90 for on-line analysis of chlorinator tail gas for chlorine. The apparatus 90 includes an enclosure 91 (preferably a NEMA-4 fiberglass enclosure, supra). Tubing 92 is used to conduct a nitrogen purge stream into the enclosure 91. Tubing 93 is used to conduct the nitrogen purge stream from the enclosure 91. The enclosure 91 contains a Servomex ultraviolet chlorine analyzer (Servomex Company, Inc., Sugarland, Tex.) comprised of a detector portion 94, a cell portion 95 and a source portion 96. Tubing 97 is used to conduct a nitrogen purge stream through a boss 95a, through a boss 95b by way of tubing 97a and then out of the enclosure 91 by way of tubing 98. The boss portions 95a and 95b of the cell 95 help protect the detector portion 94 and the source portion 96 from leaks. Electrical cables 99 and 100 provide power to and conduct an analyzer signal from the apparatus 90, which signal is a function of the chlorine concentration in the chlorinator tail gas. Conditioned chlorinator tail gas (from the apparatus shown in FIG. 2) is conducted to and from the cell portion 95 by way of one quarter inch diameter heat traced (at about ninety degrees Celsius) perfluoroalkoxy tubing 101 and 102 respectively.

It should be understood that the above description regarding the on-line analyzers relates to specific preferred systems and that the full scope of the instant invention is not limited thereby. For example, other components of interest can be analyzed on-line.

Comparative Example 1

Figure 1:
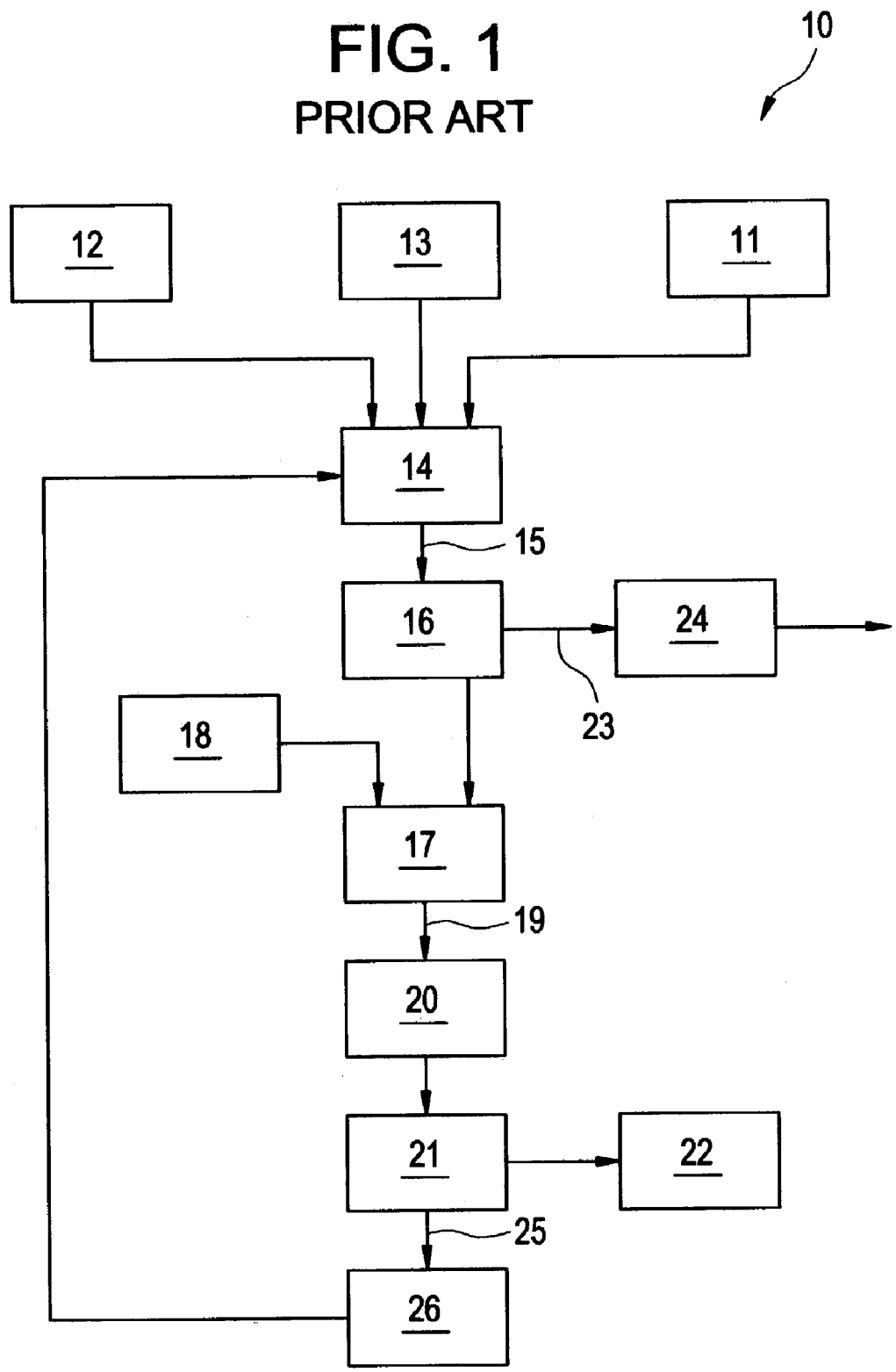
FIG. 1 is a block diagram of the prior art chloride process for producing titanium dioxide.

Referring now to FIG. 1, every hour for a twenty four hour period, a 500 milliliter gas sample bomb is used to manually withdraw a sample of burner tail gas 25. The sample bombs are taken to a laboratory and the burner tail gas is analyzed for oxygen by the Orsat test. The results are graphed as oxygen concentration versus time and show an essentially level oxygen concentration of about nine percent oxygen.

EXAMPLE 1

Referring now to FIG. 1, the burner tail gas 25 is flowed through the conditioning apparatus of FIG. 2 and then the on-line analyzer of FIG. 3 for the same twenty four hour period as COMPARATIVE EXAMPLE 1. The results are graphed as oxygen concentration versus time and show an essentially level oxygen concentration of about ten percent oxygen but also two peaks of oxygen concentration missed by the manual sampling of COMPARATIVE EXAMPLE 1. The first peak, at 9.6 hours, indicated an oxygen concentration of about sixteen percent oxygen for about ten minutes. The second peak, at 18.5 hours, indicated an oxygen concentration of about twelve percent oxygen for about ten minutes.

Comparative Example 2

Referring now to FIG. 1, every hour for a twenty four hour period (the same time period as COMPARATIVE EXAMPLE 1), a 500 milliliter gas sample bomb is used to manually withdraw a sample of burner tail gas 25. The sample bombs are taken to a laboratory and the burner tail gas is analyzed for hydrogen chloride by infrared photometry. The results are graphed as hydrogen chloride concentration versus time and show an essentially level hydrogen chloride concentration of about four percent hydrogen chloride.

EXAMPLE 2

Referring now to FIG. 1, the burner tail gas 25 is flowed through the conditioning apparatus of FIG. 2 and then the on-line analyzer of FIG. 4 for the same twenty four hour period as COMPARATIVE EXAMPLE 1. The results are graphed as hydrogen chloride concentration versus time and show an essentially level hydrogen chloride concentration of about four percent hydrogen chloride but also two variations of hydrogen chloride concentration missed by the manual sampling of COMPARATIVE EXAMPLE 2. The first variation, at 9.6 hours, indicated a hydrogen chloride concentration of about six percent hydrogen chloride for about ten minutes. The second variation, at 18.5 hours, indicated a hydrogen chloride concentration of about eight percent hydrogen chloride for about ten minutes.

Comparative Example 3

Referring now to FIG. 1, every hour for a twenty four hour period, a 500 milliliter gas sample bomb is used to manually withdraw a sample of chlorinator tail gas 23. The sample bombs are taken to a laboratory and the chlorinator tail gas is analyzed for chlorine by titration. The results are graphed as chlorine concentration versus time and show an essentially level chlorine concentration of about one hundredth percent chlorine.

EXAMPLE 3

Referring now to FIG. 1, the chlorinator tail gas 23 is flowed through the conditioning apparatus of FIG. 2 and then the on-line analyzer of FIG. 5 for the same twenty four hour period as COMPARATIVE EXAMPLE 3. The results are graphed as chlorine concentration versus time and show an essentially level chlorine concentration of about one hundredth percent chlorine but also a peak of chlorine concentration missed by the manual sampling of COMPARATIVE EXAMPLE 3. The peak, at 12.2 hours, indicated a chlorine concentration of about three tenths percent chlorine for about fifteen minutes.

What is claimed is:

1. An improved process for producing titanium dioxide by reacting a titanium dioxide ore with chlorine to produce a gaseous stream containing titanium tetrachloride, condensing titanium tetrachloride from the gaseous stream containing titanium tetrachloride to produce chlorinator tail gas, vaporizing the condensed titanium tetrachloride, reacting the vaporized titanium tetrachloride with oxygen to produce a gaseous stream containing titanium dioxide particles and chlorine, separating the titanium dioxide particles from the gaseous stream containing titanium dioxide particles and chlorine to produce burner tail gas, analyzing the chlorinator tail gas for residual chlorine to control the step of reacting the titanium dioxide ore with chlorine, wherein the improvement comprises the step of: analyzing the chlorinator tail gas for residual chlorine using an on-line chlorine analyzer wherein the chlorinator tail gas is passed through a filter and then to the on-line analyzer and wherein the chlorinator tail gas and the filter are heated to a temperature greater than fifty degrees Fahrenheit.

2. An improved process for producing titanium dioxide by reacting a titanium dioxide ore with chlorine to produce a gaseous stream containing titanium tetrachloride, condensing titanium tetrachloride from the gaseous stream containing titanium tetrachloride to produce chlorinator tail gas, vaporizing the condensed titanium tetrachloride, reacting the vaporized titanium tetrachloride with oxygen to produce a gaseous stream containing titanium dioxide particles and chlorine, separating the titanium dioxide particles from the gaseous stream containing titanium dioxide particles and chlorine to produce burner tail gas, analyzing the burner tail gas for oxygen to control the step of reacting the condensed titanium tetrachloride with oxygen, wherein the improvement comprises the step of: analyzing the burner tail gas for oxygen using an on-line oxygen analyzer wherein the burner tail gas is passed through a filter and then to the on-line analyzer and wherein the burner tail gas and the filter are heated to a temperature greater than fifty degrees Fahrenheit.

3. The improved process of claim 1, wherein the on-line chlorine analyzer is an on-line photometric chlorine analyzer.

4. The improved process of claim 2, wherein the on-line oxygen analyzer is an on-line paramagnetic oxygen analyzer.

5. The improved process of claim 2, further comprising the step of analyzing the burner tail gas for hydrogen chloride using an on-line hydrogen chloride analyzer.

6. The improved process of claim 5, wherein the on-line hydrogen chloride analyzer is an on-line photometric hydrogen chloride analyzer.

7. The improved process of any one of claims 1–6, wherein the chlorinator tail gas or the burner tail gas is passed through a filter and then to the on-line analyzer and wherein the chlorinator tail gas or the burner tail gas and the filter are heated to a temperature in the range of from ninety to one hundred and ten degrees Fahrenheit.

* * * * *